(12) United States Patent
Wiets

(10) Patent No.: US 9,020,222 B2
(45) Date of Patent: Apr. 28, 2015

(54) METHOD AND ARRANGEMENT FOR THE COMPUTER-ASSISTED STRUCTURING OF MEDICAL EXAMINATION DATA

(71) Applicant: Michael Wiets, Erlangen (DE)

(72) Inventor: Michael Wiets, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 245 days.

(21) Appl. No.: 13/682,910

(22) Filed: Nov. 21, 2012

(65) Prior Publication Data

US 2013/0129167 A1 May 23, 2013

(30) Foreign Application Priority Data

Nov. 21, 2011 (DE) .......................... 10 2011 086 724

(51) Int. Cl.
G06K 9/00 (2006.01)
G06Q 50/24 (2012.01)

(52) U.S. Cl.
CPC ...................................... G06Q 50/24 (2013.01)

(58) Field of Classification Search
USPC .................................. 382/128–134, 305, 306
See application file for complete search history.

(56) References Cited

U.S. PATENT DOCUMENTS

| 6,381,029 | B1 * | 4/2002 | Tipirneni ..................... 358/1.14 |
| 2004/0068423 | A1 | 4/2004 | Shaw |
| 2004/0141661 | A1 * | 7/2004 | Hanna et al. .................. 382/305 |
| 2006/0031236 | A1 * | 2/2006 | Isogawa et al. ............... 707/100 |
| 2012/0143625 | A1 * | 6/2012 | Eaves et al. ....................... 705/3 |

OTHER PUBLICATIONS

Digital Imaging and Communications in Medicine (DICOM), Part 5: Data Structures and Encoding, PS 3.5—2006 "Encapsulated RE compressed Images". Copyright 2006 by the National Electrical Manufacturers Association; Copyright 2006 by the National Electrical Manufacturers Association; Digital Imaging and Communications in Medicine (DICOM), Part 5: Data Structures and Encoding, PS 3.5—2006 "Encapsulated RE compressed Images". Copyright 2006 by the National Electrical Manufacturers Association; Digital Imaging and Communications in Medicine (DICOM), Part 5: Data Structures and Encoding, PS 3.5—2006 "Encapsulated RE compressed Images". Copyright 2006 by the National Electrical Manufacturers Association; Virginia 200209; National Electrical Manufacturers Association; 2006; US.

(Continued)

*Primary Examiner* — Alex Liew

(57) ABSTRACT

An arrangement for computer-assisted structuring of medical examination data is provided. The arrangement has a device for receiving at least one medical examination data record including at least one image data record created with a radiological imaging device, a device for receiving medical video data from external video sources, a device for converting the medical video data into a medical standard format in which a time stamp of the video data generation is stored, a device for storing the converted video data and the at least one examination data record, and a device for outputting the video data and examination data record. The video data and the at least one image data record can be arranged according to their time stamp.

11 Claims, 1 Drawing Sheet

(56) References Cited

OTHER PUBLICATIONS

S. Furuie et al.: Integrating Medical Images and Clinical Information. In: Fourth International Conference on Information and Communication Technology (ICICT 2006), Cairo, Proceedings of Fourth Intenational Conference on Info. and Com. Techn., p. 555-563, 2006; URL: http://www.icict.gov.eg/ICICT-2006/Papers/Electronic%20Health%20Records&20%28EHR%29/ICICT-pepsfuruie2006__06__13-final-jpeg-sem__autores.pdf (Nov. 6, 2012); 2006.

J. An et al.: Integrated Visualization of Multi-Modal Electronic Health Record Data. Proceedings of the 2nd Internat. Conf. on Bioinformatics and Biomedical Engineering, ICBEE 2008, p. 640-643; 2008.

Online-Enzyklopädie "Wikipedia", Artikel v. 26.10.2011 zum Begriff "Server", (Nov. 6, 2012); 2011; Oct. 26, 2011.

\* cited by examiner

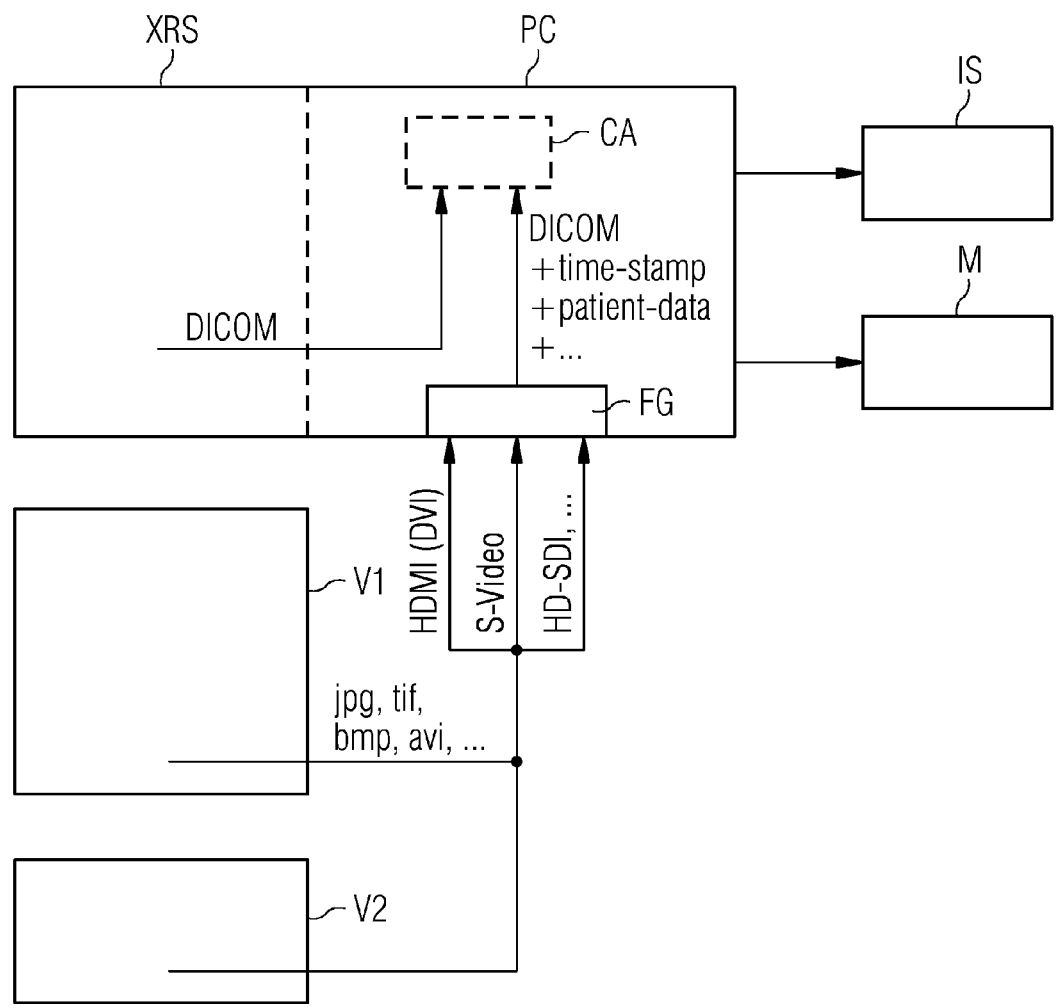

METHOD AND ARRANGEMENT FOR THE COMPUTER-ASSISTED STRUCTURING OF MEDICAL EXAMINATION DATA

CROSS REFERENCE TO RELATED APPLICATIONS

This application claims priority of German application No. 10 2011 086 724.4 filed Nov. 21, 2011, which is incorporated by reference herein in its entirety.

FIELD OF INVENTION

The application lies in the fields of medical technology and medical information technology and relates to the computer-assisted structuring of medical examination data and/or one or several examination data records.

BACKGROUND OF INVENTION

The main field of application lies inter alia in the field of radiology, in which computer-assisted RIS (Radiology Information System), HIS (Hospital Information System) and PACS (Picture Archiving and Communication System) systems are usually used. The findings are based on a medical imaging examination on different modalities, such as for instance computed tomography (CT), magnetic resonance tomography (MRT), positron emission tomography (PET), an x-ray device (x-ray) or an ultrasound device (US) The cited radiological examination devices represent the image data record. The image data record is generally an image volume data record, which contains a volume image, or an image series data record, which contains a series of images.

All incoming video signals from external sources, for instance originating from endoscopy, IVUS (Intravascular ultrasound), OCT (optical coherence tomography), ultrasound etc. were previously prepared by an external computer and then firstly output on a monitor. The necessary patient data is currently input twice (x-ray system and external computer). The image information can in the meantime be displayed adjacent to one another on modern, large-scale monitors, however this has many disadvantages. Patient information may be incorrect for instance on account of typing errors. The generation data may be incorrect. Above all, in the findings report which can also be created mechanically in order to assist the user, the correct sequence, in which the image information has been acquired, not be specified. This information is however important in the findings and/or also in the reproduction of the findings report. The image information may however not be stored in the same archive, or only with difficulty, since x-ray images in DICOM format (Digital Imaging and Communications in Medicine) are stored. Image information from external sources nevertheless exist in most instances in jpg-, bmp-, tif- or avi-format. An archiving in a PACS/HIS/KIS/RIS is rarely possible.

SUMMARY OF INVENTION

The object of the present application consists in improving the afore-cited information representation, structuring and storage of the afore-cited examination and/or findings data and video data.

The object is achieved with a method and an apparatus and/or arrangement as well as a computer program product according to the independent claims. Embodiments of the application form the subject matter of the dependent claims or can be inferred from the subsequent description and the embodiments.

The image information from external video sources is to be read in directly, e.g. via a frame grabber, into the computer of an x-ray system. In this way, it is to be converted into a format used as standard in medical technology, such as into the DICOM format. Moreover, it is provided with the time stamp of the x-ray system and is extended with the patient data likewise stored in the x-ray system. The data is to be stored in the same archive as the x-ray images. The different connection possibilities of the video sources such as for instance SVideo, HDMI (DVI), HD-SID etc. and the different image formats such as for instance jpg, bmp, tif, avi, etc. are taken into consideration here.

The application provides for an integration of the data in different data formats, wherein the process flow is accelerated and facilitated, by no longer having to type the patient information twice. The shared archive facilitates access and if applicable the mechanical sorting in the correct sequence of image acquisition.

In accordance with the prior art described in the introduction, the advantage for the physician is that he/she is not able to arrange the two separate archives correctly or only with difficulty. The disclosed introduction of the shared time stamp allows radiological and external recordings to be assigned relative to one another.

The application is also economical by only one computing system still being used. The risk of malpractice and/or unnecessary radiation load is also minimized.

A further aspect of the application is an arrangement, such as one or several servers and/or computers, for the computer-assisted structuring of medical examination data comprising device and/or modules for implementing the afore-cited method, which can be characterized in each instance in a hardware or software manner and/or as a computer program product.

The patient examination data and/or findings data and video data can be shown here on a display apparatus.

BRIEF DESCRIPTION OF THE DRAWINGS

Details and developments of the application result from the subsequent description of embodiments in conjunction with the drawings, in which: the FIGURE shows a characteristic of the disclosed arrangement.

DETAILED DESCRIPTION OF INVENTION

The FIGURE shows an embodiment of the application in the form of an architecture of a software and/or hardware implementation.

Components of the disclosed arrangement are shown in the FIGURE. A PC or computer which includes a shared archiving system CA is connected to an imaging x-ray system XRS. The computer is connected to the PACS/HIS/KIS/RIS system IS and can display data on a monitor M. Video or image data or signals of different formats, e.g. S-Video, HD, jpeg, tif, etc. from one or several external video sources, identified in the FIGURE e.g. as V1 and V2, are transmitted via a frame grabber FG connected to the archiving system CA, i.e. a video or image capture circuit, into the shared archiving system. A findings report can be manually and/or mechanically created in the computer PC from the data stored in the shared archiving system and/or saved in the PACS/HIS/KIS/RIS system. In this way, inconsistencies or redundancies in the creation of the findings report can be disclosed, if necessary made known and if necessary eliminated.

One aspect of the application lies in the use of a computer for the storage of the shared image information, both that of the x-ray system and also that of all external video sources. The aspect here is the correct time stamp or time stamp synchronized between the two recording devices, and the shared archive system to be used. It is as a result possible to temporally correctly arrange the image information from the x-ray system and the external sources. This image information can then be introduced correctly in a manually and/or mechanically created findings report. Multiple examinations (e.g. by x-rays), which represent a dose to the physician and the patient and/or even malpractice on account of an incorrect representation of the object of interest (e.g. kidneys), can be prevented. Furthermore, the same patient information is used so that a faulty examination is prevented. At the same time, the workflow or process flow is simplified within the examination. The storage into a PACS or suchlike is also enabled and/or significantly simplified on account of the integration and the DICOM format.

LIST OF REFERENCE CHARACTERS

CA shared archiving system
FG frame grabber (video- and/or image capture circuit)
IS PACS/HIS/KIS/RIS
M display apparatus and/or monitor and/or display
PC PC and/or computer
V1, V2 external video sources 1 and 2
XRS imaging x-ray system

The invention claimed is:

1. An arrangement for computer-assisted structuring a medical examination data, comprising:
   a device for receiving an image data record comprising a medical standard format created with a radiological imaging device, wherein a time stamp of the image data record generation is stored in the image data record;
   a device for receiving a medical video data comprising a different format of the image data record from external video sources;
   a device for converting the medical video data into the medical standard format and providing the time stamp of the image data record generation to the convened medical video data;
   a device for storing the converted video data and the image data record; and
   a device for outputting the converted video data and the image data record,
   wherein the converted video data and the image data record are synchronized based on the time stamp, and
   wherein the converted video data and the image data record are temporally arranged according to the time stamp.

2. The arrangement as claimed in claim 1, further comprising a device for creating a findings report from the image data record.

3. The arrangement as claimed in claim 2, further comprising a device for disclosing and/or making known inconsistencies in the findings report.

4. The arrangement as claimed in claim 2, further comprising a device for disclosing and/or eliminating redundancies in the findings report.

5. The arrangement as claimed in claim 1, wherein the medical standard format comprises DICOM format.

6. A method for computer-assisted structuring medical examination data, comprising:
   receiving an image data record comprising a medical standard format created with a radiological imaging device, wherein a time stamp of the image data record generation is stored in the image data record;
   receiving a medical video data sources comprising a different format of the image data record from external video sources;
   converting the medical video data into the medical standard format;
   providing the time stamp of the image data record generation to the converted medical video data;
   storing the convened video data and the image data record;
   synchronizing the converted video data and the image data record based on the time stamp; and
   outputting the converted video data and the image data record,
   wherein the converted video data and the image data record are temporally arranged according to the time stamp.

7. The method as claimed claim 6, further comprising creating a findings report from the image data record.

8. The method as claimed claim 7, further comprising disclosing and/or making known inconsistencies in the findings report.

9. The method as claimed claim 7, further comprising disclosing and/or eliminating redundancies in the findings report.

10. The method as claimed claim 6, wherein the medical standard format comprises DICOM format.

11. A computer for computer-assisted structuring medical examination data, comprising:
    a shared archiving system that:
       receives an image data record comprising a medical standard format created with a radiological imaging device, wherein a time stamp of the image data record generation is stored in the image data record; and
       receives a medical video data comprising a different format of the image data record from external video sources;
    a frame grabber that converts the medical video data into the medical standard format and provides the time stamp of the image data record generation to the converted medical video data;
    and
    a monitor that outputs the converted video data and the image data record,
    wherein the converted video data and the image data record are synchronized based on the time stamp and stored in the shared archiving system, and
    wherein the converted video data and the image data record are temporally arranged according to the time stamp.

* * * * *